United States Patent [19]
Wu et al.

[11] Patent Number: 5,998,658
[45] Date of Patent: Dec. 7, 1999

[54] CATALYTIC PROCESSES FOR THE PREPARATION OF ACETIC ESTERS

[75] Inventors: Kuo-Ching Wu; Ching-Tang Lin, both of Hsin-Chu, Taiwan

[73] Assignee: Industrial Technology Research Institute, Hsincho, Taiwan

[21] Appl. No.: 09/105,795

[22] Filed: Jun. 26, 1998

[51] Int. Cl.$^6$ .................................................. C07C 67/08
[52] U.S. Cl. ............................................................. 560/239
[58] Field of Search ............................................... 560/239

[56] References Cited

U.S. PATENT DOCUMENTS

| | | | |
|---|---|---|---|
| 5,235,102 | 8/1993 | Palmer et al. | 562/607 |
| 5,518,699 | 5/1996 | Kashnitz et al. | 422/211 |
| 5,719,311 | 2/1998 | Wu et al. | 560/98 |

*Primary Examiner*—Samuel Barts
*Assistant Examiner*—Rosalynd Keys
*Attorney, Agent, or Firm*—W. Wayne Liauh

[57] ABSTRACT

An improved process for the preparation of acetic esters is disclosed. It comprises a fixed bed reaction and a catalytic distillation. The fixed bed reaction comprises the steps of: (a) charging acetic acid and alcohol into a fixed bed reactor under a predetermined reaction condition; and (b) reacting the esterification reactants in the fixed bed reactor. The fixed bed reactor contains acidic catalysts that are present in a solid phase, and the reaction condition is controlled such that (i) the reactants and the products co-exist in a gas-liquid two-phase equilibrium in the fixed bed reactor and that (ii) at least one component of the reactants is present in one phase and at least one component of the products is present in another phase. The catalytic distillation comprises the steps of: (1) charging acetic acid from top of a catalytic distillation column and the reaction products from the fixed bed reactor from the bottom of the catalytic column in a counter-flow manner; and (c) continuously removing acetic ester and water from the top of the catalytic distillation column, and continuously removing acetic acid from the bottom of the catalytic distillation column. The acetic acid removed from the catalytic distillation column is fed into the fixed bed reactor. Very high alcohol conversion and essentially alcohol free product can be obtained at substantially reduced height of the catalytic distillation column.

7 Claims, No Drawings

CATALYTIC PROCESSES FOR THE PREPARATION OF ACETIC ESTERS

FIELD OF THE INVENTION

The present invention relates to an improved method for making esters of acetic acid. More specifically, the present invention relates to a catalytic distillation process utilizing solid acidic catalysts for the esterification of acetic acid with alcohols. The process disclosed in the present invention provides several distinct advantages, such as substantially improved yield, reduced waste disposal problems, and reduced production cost including substantially reduced purification cost in order to remove alcohol from the final product stream.

BACKGROUND OF THE INVENTION

U.S. Pat. No. 5,719,311, the content thereof is incorporated herein by reference, discloses a fixed bed catalytic process for the esterification of carboxylic acids and alcohols into carboxylic esters. In the process disclosed in the '311 patent, the fixed bed reactor contains acidic catalysts that are present in a solid phase, and the reaction condition is controlled such that (i) the reactants and the products co-exist in a gas-liquid two-phase equilibrium in the fixed bed reactor and that (ii) at least one component of the reactants is present in one phase and at least one component of the products is present in another phase. Very high reaction yield and selectivity, typically better than 90%, sometimes exceeding 99%, were observed with the process disclosed in the '311 for preparing the esters of Methanol/propionic acid, Methanol/methacrylic acid, isobutanol/hexahydrophthalic anhydride, and isooctyl alcohol/phthalic anhydride. However, when the carboxylic acid is acetic acid, which has high miscibility with many alcohols, the reaction yield from the process of the '311 will not be in the same high level as with other carboxylic acids, and conventional processes need to be used to produce esters of acetic acid in an economic manner. Lowered reaction yield causes unsatisfactory amounts of alcohol to remain in the production, thus, further adversely affecting the economic potential of the process, especially with regard to post-esterification purification cost.

Esters of acetic acids, or acetate, and derivatives thereof have been used in a wide variety of industrial applications, such as for use in making coatings, adhesives, perfumes, plasticizers, etc. Unsaturated carboxylic esters can also be used as monomers or intermediate raw materials in preparing resins covering a wide range of applications.

Conventionally, the processes of making acetic esters from acetic acids and alcohols can be classified into the following three main categories:

(a) Liquid-phase esterification reaction utilizing a liquid catalyst: This type of processes utilize liquid phase acid, such as sulfuric acid, phosphoric acid, sulfonic acid, or p-toluenesulfonic acid, as catalysts.

(b) Liquid phase esterification reaction utilizing a solid catalyst: This type of processes typically utilize a cationic ionic exchange resin as catalyst. Examples of this type of processes include those disclosed in Japan Laid-Open Patent Application 2-279654 and European Patent EPO-10,953.

(c) Gas phase esterification reaction: This type of processes utilize a variety of catalysts such as heteropolyacids (Japan Laid-Open Patent Application 57-99556), oxides (Japan Laid-Open Patent Application 51-76019), liquid phase acids carried by a solid carrier (UK Pat. No. 1,017,806; U.S. Pat. No. 5,151,547; Japan Laid-Open Patent Application 43-20286), and zeolite (SU 1719393) in a gas phase reaction.

One of the problems associated with the liquid-catalyst liquid-phase esterification reaction is that the acidic liquid catalysts of sulfuric acid or p-toluenesulfonic acid can cause corrosion problems to the reactor. These liquid acid catalysts are also discharged along with the reaction products, thus causing severe waste disposal and pollution problems. Furthermore, because the esterification of acetic acids involves a reversible reaction, in order to increase the conversion rate of acetic acids, either excessive amounts of alcohols must be used, or the product from the esterification reaction must be constantly removed from the reaction system. In either case, the production cost of carboxylic esters is substantially increased.

The solid-catalyst, liquid-phase esterification reaction, which typically utilizes a cationic ionic exchange resin as catalyst, ameliorates the corrosion and waste disposal problems experienced with the liquid-catalyst liquid-phase processes, and results in simplified separation procedure required between the reaction product and catalysts. However, cationic ion-exchange resins typically exhibit relatively poor heat-resistance, and they often lose substantial activity after being subject to heat. Once the catalytic activity of the cationic ion-exchange resins is reduced, it is difficult to be regenerated. Furthermore, during the solid-catalyst, liquid-phase esterification process, reaction products cannot be removed from the reaction stream so as to favorably change the reaction equilibrium, and the reaction yield can only be improved by separating unreacted reactants from the product stream and recycling the unreacted reactants. This causes the production cost to be maintained at a relatively high level.

In the gas phase esterification reaction, the reaction conditions are maintained so that all the reactants and products are in the gas phase. Typically, inorganic materials are utilized as catalysts which typically exhibit excellent heat resistance and can be easily separated from the reaction products. However, the gas phase reaction necessitates a relatively large reaction vessel, resulting in large capital investment cost. Furthermore, if the gas phase esterification reaction is utilized to produce unsaturated carboxylic esters, the high reaction temperature often causes undesired by-products of polymers or oligmers to be produced. In certain instances, the high reaction temperature has caused the alcohol molecules to be dehydrated to become ethers. These side-reactions will tend to cause the reaction catalysts to lose their activity and result in operational difficulties.

The process disclosed in the '311 patent solved many of the problems described above. However, as it is currently structured, the process disclosed in the '311 patent is not very economically attractive, and hence is not commercially applicable for the esterification of acetic acid.

U.S. Pat. No. 4,939,294 discloses a catalytic distillation process for the preparation of methyl acetate which utilizes sulfuric acid a catalyst and which requires a 72-tray catalytic distillation tower. The catalytic distillation process offers a feasible alternative to the conventional process for making methyl acetate, because the latter typically requires eight distillation towers for post-esterification separation. For ethyl acetate, which only requires three distillation towers for post-esterification purification in the conventional processes, the catalytic distillation process disclosed in the '294 using sulfuric acid as catalyst, is no longer attractive.

SUMMARY OF THE INVENTION

The primary object of the present invention is to develop an improved process for preparing esters from acetic acid and alcohols. More specifically, the primary object of the present invention is to develop an improved process for the preparation of esters from acetic acid and alcohols which eliminates or minimizes many of the problems, such as corrosion, waste disposal, generation of undesired side-products, etc., often experienced in the prior art processes. The process disclosed in the present invention also improves the service life of the catalysts used in the esterification process, reduces reaction time, and substantially increases the reaction yield. The increase in reaction yield provided by the process disclosed in the present invention reduces the effort required for post-reaction separations, and further reduces the production cost.

The process disclosed in the present invention for the esterification of acetic acid involves a two-stage process, and the first stage of the process involves a gas-liquid-solid three-phase reaction environment. The solid phase, which preferably is provided in the form of a fixed bed reactor, comprises a solid acidic catalyst whose surface is covered, via diffusion and other mass transfer mechanisms, with molecules of reaction components, which comprise both reactants (acetic acid and alcohols) and products (acetic esters and water). In the present invention, the reaction conditions are controlled such that at least one of the reaction components is present as a liquid phase and at least one of the reaction components is present as a gas phase, and the esterification reaction is accomplished through interfacial diffusion at the catalyst surface. Thermodynamically speaking, it is a well accepted terminology that a component is "present as a gas phase" when the vapor pressure of that component at the reaction temperature is greater than the reaction pressure, so that it is present thermodynamically and predominantly in the gas phase. Similarly, a component is "present as a liquid phase" when the vapor pressure of that component at the reaction temperature is lower than the reaction pressure, so that it is present thermodynamically and predominantly in the liquid phase.

In one preferred embodiment of the present invention, the reaction conditions in the first stage are controlled such that the acetic acid is present as a liquid phase, and the alcohol, acetic ester, and water are present as a gas phase. In another preferred embodiment of the process disclosed in the present invention, the reaction conditions are controlled such that acetic acid, alcohol, and acetic ester are present as liquid phase, and water is present as a gas phase. It is further preferred that all the reactants (or products) are in the same phase, while at least one of the products (or reactants) is in another phase. In all cases, of course, the acidic catalysts are present as a solid phase. One of the key elements of the present invention is that, since the reaction condition is controlled such that at least one of the reactants and at least one of the products will be in different phases, a phase change will always accompany the reaction. This concurrent phase change helps the reaction stream to maintain at a relatively uniform temperature, thus greatly reducing the degree of catalyst poisoning as well as minimizing the production of undesired by-products such as polymers/oligmers and ethers. The concurrent phase change also contributes to the extremely high reaction yield, typically better than 90%, observed in the present invention.

In the first stage of the process disclosed in the present invention, the acidic catalyst can be zeolite or zeolite/resin mixture. However, the key element of the present invention is to control the reaction condition utilizing a fixed bed of acidic catalysts so as to effectuate a phase change concurrent with the esterification reaction. The selection of catalyst is not critical. Other catalysts can also be used if they exhibit satisfactory temperature stability.

The second stage of the process of the present invention involves subjecting the reaction product from the first stage into a catalytic reaction tower. In the second stage, acetic acid is fed from the top portion of the distillation tower, and the reaction products from the three-phase reactor are fed from the lower portion. The esterification and extraction of the esterification product are conducted in a counter-flow manner in the distillation tower. The distillation tower is designed that the top distillate from the distillation tower contains less than 0.1 wt % alcohol. Acetic ester and water are continuously removed from the top of the distillation tower. Because of the low alcohol content in the top distillate, the post-esterification purification can be greatly simplified and the amount of energy consumption can also be greatly reduced. The bottom product from the distillation tower contains greater than 90 wt % acetic acid, which can be directly used in the esterification reaction with no or little pre-heating.

Unexpected superior results have been obtained from the novel process disclosed in the present invention. Because of its high energy efficiency, high reaction yield, and low catalyst waste production, the method disclosed in the present invention presents a very viable alternative to the well-established commercial processes.

DETAILED DESCRIPTION OF THE PREFERRED EMBODIMENT

The present invention discloses an improved process for the preparation of esters from acetic acid and alcohols which eliminates or minimizes many of the problems experienced in the prior art processes. The problems solved by the process disclosed in the present invention include corrosion problems, liquid waste disposal problems, productions of undesired side-products such as polymers/oligmers and ethers, etc. Other advantages of the process disclosed in the present invention include improvement in the service life of the catalysts used in the esterification process, reduction of reaction time required, the excellent reaction yield, and reduced effort required for recycling and separation. The process disclosed in the present invention also achieves substantial energy savings in the post-esterification purification.

In the present invention a two-stage process is disclosed for improving the esterification yield from acetic acid. The first stage, which involves a three-phase reaction for the esterification of acetic acids, comprises a solid phase, and a liquid phase which is in equilibrium with a gas phase. The solid phase, which preferably is provided in the form of a fixed bed reactor, comprises a solid acidic catalyst whose surface is covered, via diffusion and other mass transfer mechanisms, with molecules in a reaction stream, which comprise both reactants (carboxylic acids and alcohols) and products (carboxylic esters and water). The acidic catalyst can be zeolite or a zeolite/resin mixture. However, the selection of the acidic catalysts is not critical. Other catalysts can also be utilized if they exhibit satisfactory temperature stability.

In the second stage, a catalytic distillation tower is utilized which contains a solid catalyst. Acetic acid is fed from the top portion of the distillation tower, and the reaction products from the three-phase reactor are fed from the lower portion. The esterification and extraction of the esterification product are conducted in a counter-flow manner in the distillation tower. The distillation tower is designed that the top distillate from the distillation tower contains less than 0.1 wt % alcohol. Acetic ester and water are continuously removed from the top of the distillation tower. Because of the low alcohol content in the top distillate, the post-esterification purification can be greatly simplified and the amount of energy consumption can also be greatly reduced. The bottom product from the distillation tower contains greater than 90 wt % acetic acid, which can be directly used in the esterification reaction with no or little pre-heating.

One of the key elements of the first stage of the present invention is to control the reaction conditions so that at least one of the components in the reaction stream is present as a liquid phase and at least one of the components in the reaction stream is present as a gas phase, and the esterification reaction is accomplished through interfacial diffusion and other mass transfer mechanisms at the catalyst surface. A component is defined as being "present as a gas phase" when the vapor pressure of that component at the reaction temperature is greater than the reaction pressure, so that it is present, thermodynamically speaking, in the gas phase. Similarly, a component is defined as being "present as a liquid phase" when the vapor pressure of that component at the reaction temperature is less than the reaction pressure, so that it is present thermodynamically predominantly in the liquid phase. In one preferred embodiment of the present invention, the reaction conditions are controlled such that the carboxylic acid is present as a liquid phase, and the alcohol, carboxylic ester, and water are present as a gas phase. In another preferred embodiment of the process disclosed in the present invention, the reaction conditions are controlled such that carboxylic acid, alcohol, and carboxylic ester are present as liquid phase, and water is present as a gas phase. It is further preferred that all the products are in the same phase, while at least one of the reactants is in another phase. In all cases, the acidic catalysts are present as a solid phase.

By combination the three-phase esterification reaction of the first stage of the present invention with the catalytic distillation of the second stage of the present invention, unexpectedly superior results can be obtained for preparing acetic esters, in terms of high yield and greatly simplified post-esterification purification. The present invention also results in substantial energy savings.

In the present invention, the conversion, yield, and selectivity are defined as follows. These definitions are consistent with those that have been conventionally accepted.

$$\text{conversion (mol \%)} = \frac{\text{moles of alcohol in the feed} - \text{moles of alcohol in the product}}{\text{moles of alcohol in the feed}} \times 100\%$$

$$\text{selectivity (mol \%)} = \frac{\text{moles of acetic ester in the product}}{\text{moles of alcohol in the feed} - \text{moles of alcohol in the product}} \times 100\%$$

$$\text{yield (mol \%)} = \frac{\text{moles of acetate in the product}}{\text{moles of alcohol in the feed}} \times 100\%$$

The present invention will now be described more specifically with reference to the following examples. It is to be noted that the following descriptions of examples, including the preferred embodiment of this invention, are presented herein for purposes of illustration and description, and are not intended to be exhaustive or to limit the invention to the precise form disclosed.

EXAMPLE 1

200 g of $ZrOCl_2 \cdot 8H_2O$ was dissolved in 2.5 liters of water, into which ammonia water was gradually added in the presence of a pH meter. The addition of ammonia water was stopped when the pH meter read 10, and the mixture was stirred for 30 minutes then lied still for 24 hours. The precipitates were rinsed with deionized water to remove all the chloride ions (as measured using 0.1 N $AgNO_3$ titration until no precipitate was observed), filtered and dried at 100° C. for 24 hours.

50 g of the precipitates obtained above were mixed with 750 ml of 1 N sulfuric acid, stirred for 3 hours and filtered. The filter cake was dried at 110° C. for 24 hours, and calcined at 650° C. in the presence of air for 3 hours. The final product was a $SO_4^{=/ZrO}{}_2$ catalyst. The $SO_4^{=/ZrO}{}_2$ catalyst obtained above was crushed and 7 ml of the crushed $SO_4^{=/ZrO}{}_2$ catalysts at 30–40 mesh were placed inside a ⅜ stainless steel tube to form a fixed bed reactor.

A reactant composition containing ethanol and acetic acid at an alcohol/acid mole ratio of 1 was prepared and charged into the fixed bed reactor from the upper portion thereof at a feed velocity LHSV (liquid hourly space velocity)=1 $hr^{-1}$. The temperature of the fixed bed reactor was controlled at 110° C., and the pressure of the fixed bed reactor was maintained such that the acetic acid was in the liquid phase, and ethanol, ethyl acetate, and water (the latter two are reaction products) were in the gas phase. After the reaction was completed in the fixed bed reactor, the reaction product flowed out of the fixed bed reactor, cooled and collected in a collecting vessel. The liquid product was analyzed using a gas chromatography, and the results are summarized in Table 1:

TABLE 1

| | |
|---|---|
| Reaction temperature (° C.) | 110 |
| alcohol/acid mole ratio | 1 |
| LHSV ($hr^{-1}$) | 1 |
| Conversion of ethanol (mol %) | 85.27 |
| Selectivity of ethyl acetate (mol %) | 99.57 |

Table 1 shows that while excellent selectivity (99.57%) was obtained, the conversion from ethanol was only 85.27 mol %.

EXAMPLE 2

7 ml of Nafion NR-50 catalysts (from Mobil Oil) were placed inside a ⅜ stainless steel tube to form a fixed bed reactor. A reactant composition containing n-butanol and acetic acid at an alcohol/acid mole ratio of 1 was prepared and charged into the fixed bed reactor from the upper portion thereof at a feed velocity LHSV (liquid hourly space velocity)=1 $hr^{-1}$. The temperature of the fixed bed reactor was controlled at 110° C., and the pressure of the fixed bed reactor was maintained such that the acetic acid, n-butanol, and n-butylacetate were in the liquid phase, and water was in the gas phase. After the reaction was completed in the fixed bed reactor, the reaction product flowed out of the fixed bed reactor, cooled and collected in a collecting vessel. The liquid product was analyzed using a gas chromatography, and the results are summarized in Table 1:

TABLE 2

| | |
|---|---|
| Reaction temperature (° C.) | 110 |
| alcohol/acid mole ratio | 1 |
| LHSV ($hr^{-1}$) | 1 |
| Conversion of ethanol (mol %) | 85.32 |
| Selectivity of ethyl acetate (mol %) | 99.47 |

Table 2 shows that, again, while excellent selectivity (99.47%) was obtained, the conversion from ethanol was only 85.32 mol %. Although the conversion is high, it still requires purification.

EXAMPLE 3–9

In an aqueous solution containing 20 g of $Al_2(SO_4)_3 \cdot 18H_2O$, 180 g of another aqueous solution contain sodium silicate (water glass) and 3 g of tetrapropyl ammonium bromide were added. The second aqueous solution was prepared such that the mole ratio between silicon oxide and aluminum oxide in the final mixture would be 30. The pH of the mixture was properly adjusted by adding drops of sulfuric acid. After reacting at 160–180° C. in a 2-liter high-pressure vessel for 24 hours, the reaction product was removed from the reactor, filtered, rinsed, and baked at 500° C. for 12 hours. The reaction product was aNaZSM-5 solid, which was subject to an ion-exchange process at 80° C. in ammonium nitrate solution to form $NH_4ZSM$-5. After calcining at 550° C. for 12 hours, the $NH_4ZSM$-5 solid became HZSM-5 zeolite. The HZSM-5 zeolite obtained above was crushed and 7 ml of the crushed HZSM-5 zeolite at 30–40 mesh were placed inside a 3/8 stainless steel tube to form a fixed bed reactor.

A reactant composition containing n-butanol and acetic acid at an acid/alcohol mole ratio of 1.5 was charged into the fixed bed reactor from the upper portion thereof at a feed velocity LHSV (liquid hourly space velocity)=1 $hr^{-1}$. The temperatures of the fixed bed reactor were controlled at 94, 98, 102, 106, 110, 114, and 118° C., respectively, and the pressure of the fixed bed reactor was maintained such that the acetic acid was in the liquid phase. After the reaction was completed in the fixed bed reactor, the reaction product flowed out of the fixed bed reactor, cooled, and collected in a collecting vessel. The liquid product was analyzed using a gas chromatography, and the results are summarized in Table 3:

TABLE 3

| Example | 3 | 4 | 5 | 6 | 7 | 8 | 9 |
|---|---|---|---|---|---|---|---|
| Reaction temperature (° C.) | 94 | 98 | 102 | 106 | 110 | 114 | 118 |
| acid/alcohol mole ratio | 1.5 | 1.5 | 1.5 | 1.5 | 1.5 | 1.5 | 1.5 |
| LHSV ($hr^{-1}$) | 1 | 1 | 1 | 1 | 1 | 1 | 1 |
| Conversion of alcohol (mol %) | 85.31 | 92.37 | 94.45 | 95.29 | 95.64 | 95.98 | 95.92 |
| Selectivity of n-butylacetate (mol %) | 99.93 | 99.88 | 99.71 | 99.96 | 99.78 | 99.75 | 99.81 |

Table 3 shows that while excellent selectivity was obtained in all cases, the alcohol conversion reached a maximum of 95.98 mol % at 114° C.

EXAMPLES 10–12

7ml of Amberlite IR-120 catalysts (from Aldrich Chemical Co.) were placed inside a 3/8 stainless steel tube to form a fixed bed reactor. Reactant compositions containing ethanol and acetic acid at an acid/alcohol mole ratio of 1.5, with water contents of 0, 5, and 10 wt %, respectively, were charged into the fixed bed reactor from the upper portion thereof at a feed velocity LHSV (liquid hourly space velocity)=1 $hr^{-1}$. The temperature of the fixed bed reactor was controlled at 110° C., and the pressure of the fixed bed reactor was maintained such that the acetic acid was in the liquid phase, and ethanol, ethyl acetate and water were in the gas phase. After the reaction was completed in the fixed bed reactor, the reaction product was flowed out of the fixed bed reactor, cooled, and collected in a collecting vessel. The liquid product was analyzed using a gas chromatography, and the results are summarized in Table 4:

TABLE 4

| Example | 10 | 11 | 12 |
|---|---|---|---|
| Reaction temperature (° C.) | 110 | 110 | 110 |
| acid/alcohol mole ratio | 1.5 | 1.5 | 1.5 |
| LHSV ($hr^{-1}$) | 1 | 1 | 1 |
| Conversion of alcohol (mol %) | 95.89 | 92.55 | 90.44 |
| Selectivity of n-butylacetate (mol %) | 99.48 | 99.51 | 99.31 |

Table 4 shows that while excellent selectivity was obtained in all cases, the best alcohol conversion reached a maximum of 95.89 mol % with the case which contained no water in the reactant stream. The amount of alcohol in the product stream, though small, requires a relatively expensive post-esterification purification process.

EXAMPLE 13

This Example involved a fixed-bed reaction connected in series with a catalytic distillation tower. 100 ml of Amberlite IR-120 catalysts (from Aldrich Chemical Co.) were placed inside a 1" stainless steel tube to form a fixed bed reactor. Another 100 ml of Amberlite IR-120 catalysts (also from Aldrich Chemical Co.) were placed inside a 1" distillation column to form a catalytic distillation column. Acetic acid was fed into the top portion of the catalytic distillation column at a rate of 56.6 g/hr, and product stream from the fixed bed reactor was fed into the bottom portion of the catalytic column at a rate of 103 g/hr. Acetic acid solution (which contained about 95 wt % acetic acid), which was discharged from the bottom of the catalytic distillation column at a rate of 59.6 g/hr, was mixed with a fresh ethanol stream, charged at a rate of 43.4 g/hr, and the mixture was fed into the top of the fixed bed reactor. The temperature of the fixed bed reactor was controlled at 110° C., and the pressure of the fixed bed reactor was maintained such that the acetic acid was in the liquid phase, and ethanol, ethyl acetate and water were in the gas phase. The reaction product from the fixed bed reactor was fed into the catalytic distillation column from the bottom thereof. The esterification product was collected at the top of the distillation column. After cooling the esterification product was analyzed using a gas chromatography, and the results are summarized in Table 5:

TABLE 5

| Position at the Catalytic Distillation Column | Ethanol Feed | Acetic Acid Feed | Acetic Ester Feed | Bottom Discharge | Top Discharge (Organic Layer) | Top Discharge (Aqueous Layer) |
|---|---|---|---|---|---|---|
| Flow Rate (g/hr) | 43.4 | 56.6 | 103 | 59.6 | 85.2 | 14.8 |
| Composition (wt %) | | | | | | |
| Acetic acid | — | >99.8 | 7.70 | 94.97 | — | — |
| ethanol | >99.8 | — | 5.91 | — | — | <0.01 |
| ethyl acetate | — | — | 71.48 | — | 96.36 | 6.28 |
| Water | — | — | 14.91 | 5.03 | 3.64 | 93.72 |

Table 5 shows that there was no ethanol in the organic layer of the top discharge stream. It should be noted that the same amount of catalyst was used in the catalytic distillation column as in the fixed bed reactor. Thus, the present invention was able to achieve excellent esterification yield and provide post esterification purification with substantially reduced height of the distillation column.

EXAMPLE 14

This Example also involved a fixed-bed reaction connected in series with a catalytic distillation tower. 100 ml of HZSM-5 catalysts (from Degussa Co.) were placed inside a 1" stainless steel tube to form a fixed bed reactor. Another 100 ml of 100 ml of HZSM-5 catalysts (also from Degussa Co.) were placed inside a 1" distillation column to form a catalytic distillation column. Acetic acid was fed into the top portion of the catalytic distillation column at a rate of 44.76 g/hr, and the product stream from the fixed bed reactor was fed into the bottom portion of the catalytic column at a rate of 102.36 g/hr. Acetic acid solution (which contained about 95 wt % acetic acid), which was discharged from the bottom of the catalytic distillation column at a rate of 47.12 g/hr, was mixed with fresh n-butanol, which was charged at a rate of 55.24 g/hr, and the mixture was fed into the top of the fixed bed reactor. The temperature of the fixed bed reactor was controlled at 110° C., and the pressure of the fixed bed reactor was maintained such that the acetic acid, n-butanol, and n-butyl acetate were in the liquid phase, and water was in the gas phase. The reaction product from the fixed bed reactor was fed into the catalytic distillation column from the bottom thereof. The esterification product was collected at the top of the distillation column. After cooling the esterification product was analyzed using a gas chromatography, and the results are summarized in Table 6:

TABLE 6

| Position at the Catalytic Distillation Column | n-Butanol Feed | Acetic Acid Feed | Acetic Ester Feed | Bottom Discharge | Top Discharge (Organic Layer) | Top Discharge (Aqueous Layer) |
|---|---|---|---|---|---|---|
| Flow Rate (g/hr) | 55.24 | 44.76 | 102.36 | 47.12 | 75.8 | 24.2 |
| Composition (wt %) | | | | | | |
| Acetic acid | — | >99.8 | 6.11 | 94.99 | — | — |
| ethanol | >99.8 | — | 7.54 | — | — | <0.01 |
| ethyl acetate | — | — | 74.76 | — | 99.8 | 0.68 |
| Water | — | — | 13.95 | 5.01 | 1.2 | 99.32 |

Table 6 shows that, similar to Table 5, there was no ethanol in the organic layer in the top discharge stream. It should also be noted that the same amount of catalyst was used in the catalytic distillation column as in the fixed bed reactor. Thus, the present invention was able to achieve excellent esterification yield and provide post esterification purification with substantially reduced height of the distillation column.

The foregoing description of the preferred embodiments of this invention has been presented for purposes of illustration and description. Obvious modifications or variations are possible in light of the above teaching. The embodiments were chosen and described to provide the best illustration of the principles of this invention and its practical application to thereby enable those skilled in the art to utilize the invention in various embodiments and with various modifications as are suited to the particular use contemplated. All such modifications and variations are within the scope of the present invention as determined by the appended claims when interpreted in accordance with the breadth to which they are fairly, legally, and equitably entitled.

What is claimed is:

1. A process for preparing acetic esters comprising a fixed bed catalytic esterification connected with a catalytic distillation;

wherein said fixed bed catalytic esterification comprises the steps of:
(a) charging esterification reactants, which comprise at least one alcohol and acetic acid or acetic anhydride, into a fixed bed reactor under a predetermined reaction condition;
(b) reacting said esterification reactants in said fixed bed reactor to form reaction products which comprise acetic ester and water;
(c) wherein said fixed bed reactor comprises acidic catalysts that are present in a solid phase;
(d) further wherein said reaction condition is controlled such that (i) said reactants and said products co-exist in a gas-liquid two-phase equilibrium in said fixed bed reactor and that (ii) at least one component of said reactants is present in one phase and at least one component of said products is present in another phase;

and said catalytic distillation comprises the steps of:
(a) obtaining a catalytic distillation column containing at least one acidic catalyst in a solid phase;
(b) charging acetic acid into a top of said catalytic distillation column and charging said reaction products from said fixed bed reactor into a bottom of said catalytic distillation column, wherein said catalytic distillation column is maintained at a condition so as to cause said reaction products to flow upward and said acetic acid to flow downward in a counter-flow manner;
(c) continuously removing acetic ester and water from the top of said catalytic distillation column, and continuously removing acetic acid from the bottom of said catalytic distillation column, wherein said acetic acid removed from said catalytic distillation column is fed into said fixed bed reactor.

2. The process for preparing esterification products according to claim 1 wherein said alcohols are selected from the group consisting of straight-chain, branched and aromatic alcohols having a carbon number from C1–C12.

3. The process for preparing esterification products according to claim 1 wherein said acidic catalyst comprises at least one member selected from the group consisting of oxides, zeolites, and resins.

4. The process for preparing esterification products according to claim 1 wherein said alcohol is ethanol or n-butanol.

5. The process for preparing esterification products according to claim 1 wherein catalyst comprises a $SO_4^{=}/ZrO_2$ oxide.

6. The process for preparing esterification products according to claim 1 wherein catalyst comprises a HZSM-5 zeolite.

7. The process for preparing esterification products according to claim 1 wherein catalyst comprises an amberlite catalyst.

* * * * *

UNITED STATES PATENT AND TRADEMARK OFFICE
CERTIFICATE OF CORRECTION

PATENT NO.   : 5,998,658
DATED        : December 7, 1999
INVENTOR(S)  : Kuo-Ching Wu and Ching-Tang Lin Page 1 of 1

It is certified that error appears in the above-identified patent and that said Letters Patent is hereby corrected as shown below:

<u>Title page,</u>
Item [73], insert a second assignee:
-- Lee Chang Yung Chemical Industry Corp.
   83 Pateh Road, Sec. 4, Taipei, Taiwan --

Signed and Sealed this

Fourth Day of June, 2002

*Attest:*

*Attesting Officer*

JAMES E. ROGAN
*Director of the United States Patent and Trademark Office*